United States Patent
Getty

(10) Patent No.: US 8,493,437 B2
(45) Date of Patent: Jul. 23, 2013

(54) METHODS AND SYSTEMS FOR MARKING STEREO PAIRS OF IMAGES

(75) Inventor: David Getty, Bedford, MA (US)

(73) Assignee: Raytheon BBN Technologies Corp., Cambridge, MA (US)

(*) Notice: Subject to any disclaimer, the term of this patent is extended or adjusted under 35 U.S.C. 154(b) by 869 days.

(21) Appl. No.: 12/332,508

(22) Filed: Dec. 11, 2008

(65) Prior Publication Data

US 2009/0147074 A1 Jun. 11, 2009

Related U.S. Application Data

(63) Continuation of application No. PCT/US2008/085904, filed on Dec. 8, 2008.

(60) Provisional application No. 61/007,378, filed on Dec. 11, 2007.

(51) Int. Cl.
*H04N 15/00* (2006.01)

(52) U.S. Cl.
USPC .............. 348/51; 348/151; 382/128; 382/154

(58) Field of Classification Search
USPC .............................. 348/51, 151; 382/128, 154
See application file for complete search history.

(56) References Cited

U.S. PATENT DOCUMENTS

| 6,697,506 B1* | 2/2004 | Qian et al. | 382/128 |
| 2006/0100507 A1* | 5/2006 | Mertelmeier | 600/425 |
| 2009/0080765 A1* | 3/2009 | Bernard et al. | 382/154 |
| 2009/0087067 A1* | 4/2009 | Khorasani | 382/132 |

* cited by examiner

*Primary Examiner* — Liangche A Wang
*Assistant Examiner* — Cheikh Ndiaye
(74) *Attorney, Agent, or Firm* — Ropes & Gray LLP

(57) ABSTRACT

Systems and methods for marking stereo pairs of images include an imaging device for retrieving a collection of images that are representative of a volume, where the images can be representative of a physical volume or a volumetric set of data. A computing machine identifies image elements within the retrieved collection of images representative of a volumetric set of data, and further generates image element values that are based in part on the identified image elements. The computing machine further generates a stereoscopic pair of projection images having two members, where each member of the pair is based in part on at least one image element value generated by the computing machine. A viewing apparatus displays either the calculated stereoscopic pair of projection images or a pair of stereo images selected from images representative of a physical volume, such that when the pair of images are viewed through a portion of the viewing apparatus, the resultant display is a perceived three dimensional image. An input device or computer application is further used to position a marker within the stereoscopic pair of projection images to identify a location within the stereo pair of images.

27 Claims, 10 Drawing Sheets

METHODS AND SYSTEMS FOR MARKING STEREO PAIRS OF IMAGES

FIELD OF THE INVENTION

This application relates generally to marking stereo pairs of images.

BACKGROUND OF THE INVENTION

Current techniques for stereoscopic viewing through three-dimensional objects or spaces require the generation of stereo pairs of projection images through the object or space and use of a display system that supports visual fusion of the stereo image pair. One technique for generating the stereo pair is to acquire the images directly, e.g., by x-ray imaging through the object or volume. Another approach is to generate cross-sectional images through the object or volume utilizing tomographic imaging. The stereo pair of projection images is then obtained by ray tracing through the stacked two-dimensional images. This technique further includes viewing each cross-sectional slice image sequentially or in cine mode.

Methods exist for marking two dimensional and perceived three dimensional images. Such methods include providing either a two dimensional or three dimensional cursor that can be placed within the image to mark a particular location.

SUMMARY OF THE INVENTION

In one aspect, described is a method for marking stereo pairs of images. This method includes retrieving a collection of images representative of a volume, and further identifying image elements within the retrieved collection of images. Image element values are generated based on the identified image elements. A stereoscopic pair of projection images is also generated, where each member of the stereoscopic pair of projection images is based in part on at least one image element value. The stereoscopic pair of projection of projection images is displayed such that the stereoscopic pair of projection images, when viewed through a viewing apparatus, forms a perceived three dimensional image. An input device or software application can then be used to position a marker within the stereoscopic pair of projection images to identify a location within the perceived three dimensional images.

In one embodiment, positioning the marker within the perceived three dimensional image further includes positioning at least one stereo cursor within the perceived three dimensional image. The marker may be positioned either by the user using an input device or by a computer software application (e.g., a computer aided detection algorithm).

In another embodiment, the method further includes retrieving coordinates representative of the location identified by the at least one marker. Retrieving the coordinates can, in one embodiment, be done automatically via a computer application. In each instance, the coordinates received are representative of the location identified by the marker, or the at least one stereo cursor.

Still another embodiment includes positioning a first marker and a second marker within the perceived three dimensional image to identify two locations within the three dimensional image. The first and second markers are, in one embodiment, positioned by the user using an input device. In another embodiment, the first and second markers are positioned automatically via a computer aided detection application. In another embodiment, a value representative of a length extending from the first marker to the second marker is determined. In still another embodiment, the value is determined by an application executing on a computing machine.

One embodiment includes positioning a first marker, a second marker and a third marker within the three dimensional image such that each of the first marker, the second marker and the third marker identify at least a location within the three dimensional image. The first, second and third markers are in one embodiment, positioned by the user using an input device. In another embodiment, the first, second and third markers are positioned automatically via a computer aided detection application. In another embodiment, a value representative of a volume located within an area bounded in part by the first marker, the second marker and the third marker is determined. In still another embodiment, the value is determined by an application executing on a computing machine.

In another aspect, a system for marking stereo pairs of images includes an imaging machine that retrieves a collection of images that are representative of a volume. Further included is a computing machine that is in communication with the imaging machine. The computing machine generates image element values that are based on image elements that are identified within the collection of images retrieved by the imaging machine. The computing machine also generates a stereoscopic pair of projection images, where each member of the stereoscopic pair of projection images is based in part on at least one image element value. In communication with the computing machine is a viewing apparatus that displays the stereoscopic pair of projection images such that the stereoscopic pair of projection images induces perception of a three dimensional image. Also in communication with the computing machine is an input device that positions a marker within the stereoscopic pair of projection images to identify a location within the perceived three dimensional images.

BRIEF DESCRIPTION OF THE DRAWINGS

The following figures depict certain illustrative embodiments of a method and system for three dimensional viewing, where like reference numerals refer to like elements. Each depicted embodiment is illustrative of the method and system and not limiting.

DETAILED DESCRIPTION

Figure 1:
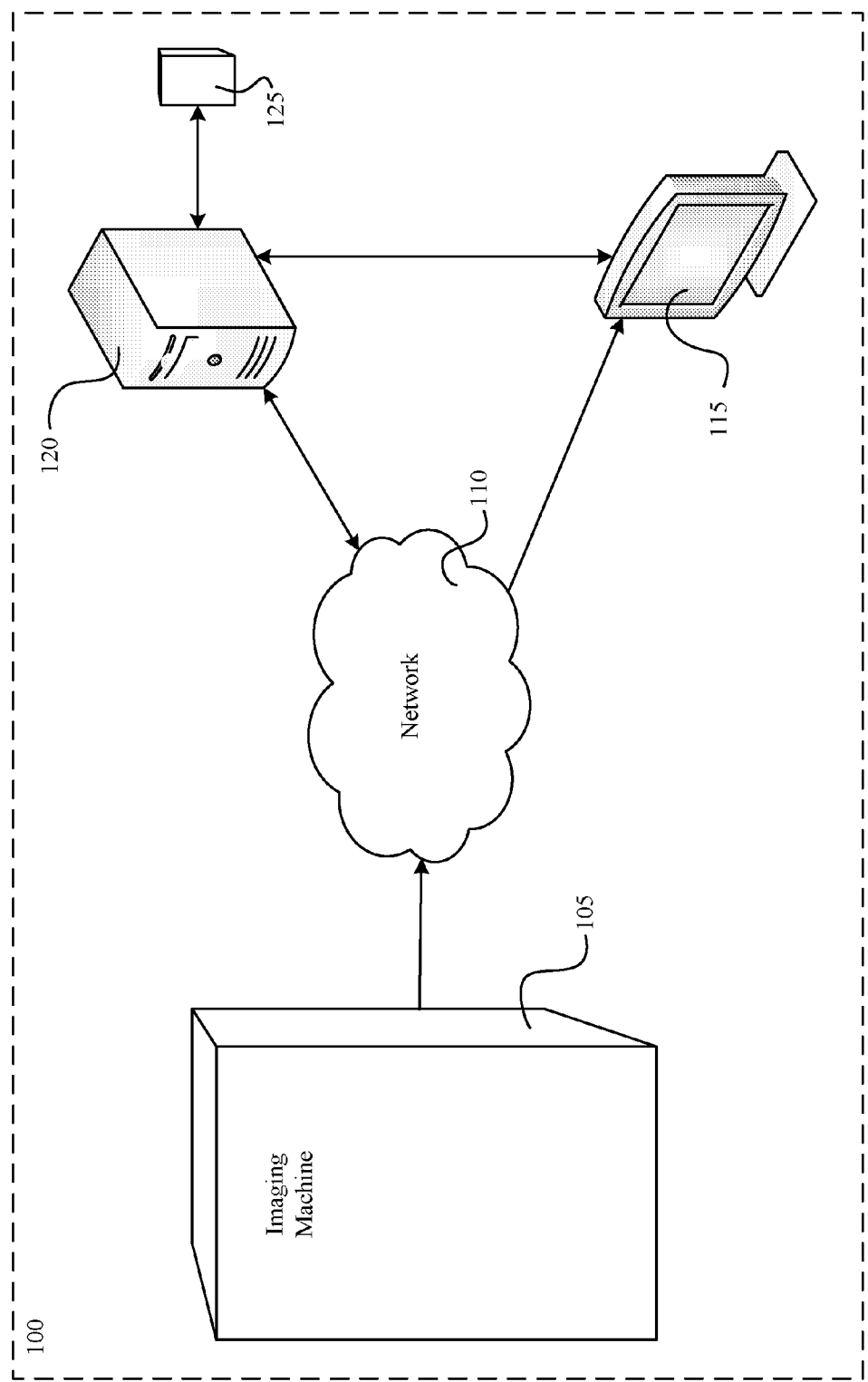
FIG. 1 depicts an embodiment of an environment for creating, processing and viewing images.

Illustrated in FIG. 1 is one embodiment of an environment 100 for creating, processing and viewing images captured by an imaging machine 105 included within the environment 100. The imaging machine 105 operates to generate image data and further transfer that data to a computing machine 120 within the environment 100. Image data is transferred to the computing machine 120 and to a viewing apparatus 115 within the environment 100, via a network 110. The viewing apparatus 115 is further connected to the computing machine 120, which is further connected to an input device 125.

Referring to FIG. 1, and in more detail, the imaging machine 105 is, in some embodiments, a breast tomosynthesis imaging unit able to produce digital images of breast tissue from those images of the breast taken during a mammogram. In particular, the breast tomosynthesis imaging unit acquires multiple projections of the breast, taken from a narrow range of angles. These projections are created by rotating an x-ray tube and detector mounted to a C-arm, around a static and compressed breast and over an angular range of 10 to 40 or more degrees. As the x-ray tube traverses the compressed breast in angular intervals within the 10 to 40 or more degree range; the x-ray tube pulses, emits radiation, multiple times, and at equally spaced intervals, during traversal of the breast. Anywhere from 0 to 30 or more projections may result from pulsing the x-ray tube during traversal around the compressed breast, and together the projections constitute a tomosynthesis projection set. Pairs of these projection images may be used as stereo pairs to generate a perceived three dimensional image. In addition, the breast tomosynthesis imaging unit reconstructs the projections within the tomosynthesis projection set using a back-projection algorithm. Each image is reconstructed in a plane parallel to the breast compression plate, and what results is a transformation of the tomosynthesis projection set into a volumetric stack of reconstructed slices. Stereo pairs of projections through the reconstructed slices may be used to generate a perceived three dimensional image.

Other embodiments include an imaging machine 105 that is a computed axial tomography (CT) scanner. In this embodiment, the volumetric data set captured by the CT scanner, once reconstructed into image slices representative of a section of the captured organ, may be further processed by components within the system 100 to create both non-stereo and stereo images. Still other embodiments include an imaging machine 105 that is any of the following types of CT scanners: electron beam CT scanner; spiral CT scanner; multi-slice CT scanner; dual source CT scanner; 256 slice CT scanner; inverse geometry CT scanner; and any other type of imaging device that utilizes volumetric x-ray data to generate a perceived three dimensional image of the object illustrated within the volumetric x-ray data. Still further embodiments include an imaging machine that is any one of the following types of technology: any type or form of magnetic resonance imaging (MRI); positron emission tomography (PET); thermal tomography; infrared imaging; three dimensional ultrasound; or any other type of modality producing a volumetric data set able to be formatted via the systems and methods discussed herein.

Still referring to FIG. 1, the imaging machine 105 communicates with a computing machine 120 via a network 110. The computing machine 120 can, in some embodiments, be any of the following: a personal computer; a client; a server; a windows-based terminal; an informational appliance; a workstation; a minicomputer; a main-frame computer; or any other computing device able to carry out those systems and methods herein described. In one embodiment, the computing machine 120 includes each of the following components: a processor (not shown); volatile memory (not shown); an operating system (not shown); a persistent storage memory (not shown); and a network interface card (not shown). Other embodiments include a computing machine 120 with any combination of the above mentioned computing components, and/or additional computing components. The processor (not shown) can, in some embodiments, include a single core, dual core, or multi-core processor. One embodiment includes a computing machine 120 that executes any of the following operating systems (not shown): any version of the WINDOWS OS; any version of the LINUX OS; any version of UNIX; any type or version of embedded operating system; any version of MAC OS; and any other type or version of operating system able to control the operation of the components included within the computing machine 120. One embodiment includes a computing machine 120 integrated into the imaging machine 105 such that the imaging machine 105 communicates directly with the viewing apparatus 115, and the input device 125 communicates with the imaging machine 105.

In one embodiment, the imaging machine 105 communicates with the computing machine 120 and viewing apparatus 115 via a network 110. This embodiment includes a network 110 that can be any of the following network types or forms: a serial network; a parallel network; a token ring network; a local-area-network (LAN); a wide-area-network (WAN); a personal area network (PAN); a private network; a public network; a packet switched network; or any other network type or form able to carry out the systems and methods herein described. Other embodiments include a network 110 that establishes connections via any of the following protocols: TCP/IP; IPX; SPX; NetBIOS; NetBEUI; SONET; SDH; T/TCP; TCPSACK; TCP-Vegas; UDP over IP; WiFi protocols such as 802.11A, 802.11B, 802.11G, or 802.11N; Bluetooth® or any other short-range communication protocol; RS-232; RS-485; or any other network protocol able to carry out the systems and methods herein described. One embodiment includes an imaging machine 105 that communicates with the computing machine 120 over a multi-user network, while other embodiments include an imaging machine 105 that communicates over a network that includes only those devices within the environment 100. In one embodiment, the network 110 includes a single wire installed between the imaging machine 105 and the computing machine 120, and/or a single wire installed between the imaging machine 105 and the viewing apparatus 115. Still other embodiments include an environment 100 where a network 110 is installed between the imaging machine 105 and the computing machine 120 that excludes the viewing apparatus 115, while other embodiments include an environment 100 where a network 110 is installed between the imaging machine 105 and the viewing apparatus 115 that excludes the computing machine 120.

The computing machine 120, in some embodiments, is connected to an input device 125 able to control the display of images on the viewing apparatus 115. In some embodiments, the input device 125 can be used to control any of the following: image contrast; grayscale; image brightness; point of view within a stereo view; tilt of the image about an axis; movement through the image or composition of image slices; magnification of portions of the image; selection of areas within the image; or any other aspect relative to the display of the image. The input device 125, in one embodiment, can be any of the following components either in combination or alone: a mouse; a keyboard; an infrared pointing device; a laser pointer; a keypad; a joystick; a stylus and tablet, where contact between the stylus and tablet generates an input signal representative of the location of the contact between the stylus and the tablet; and any other input device compatible with the system and method herein described. In one embodiment, the input device 125 is a controller with multiple degrees of freedom, and/or a controller that includes any of the following sensors either in combination or along: a tilt sensor; an accelerometer; a gyroscope; an infrared sensor; an inertial measurement unit (IMU); or any other sensor able to capture the movement of the controller over multiple degrees of freedom. Still other embodiments include an input device 125 that allows for haptic feedback. In one embodiment, the input device 125 communicates either via physical connection or wirelessly with any of the computing machine 120, the imaging machine 105, the viewing apparatus 115, or any other device included within the environment 100. Further embodiments include an input device 125 that communicates with an imaging machine 105 via the viewing apparatus 115 and network 110.

Figure 2A:
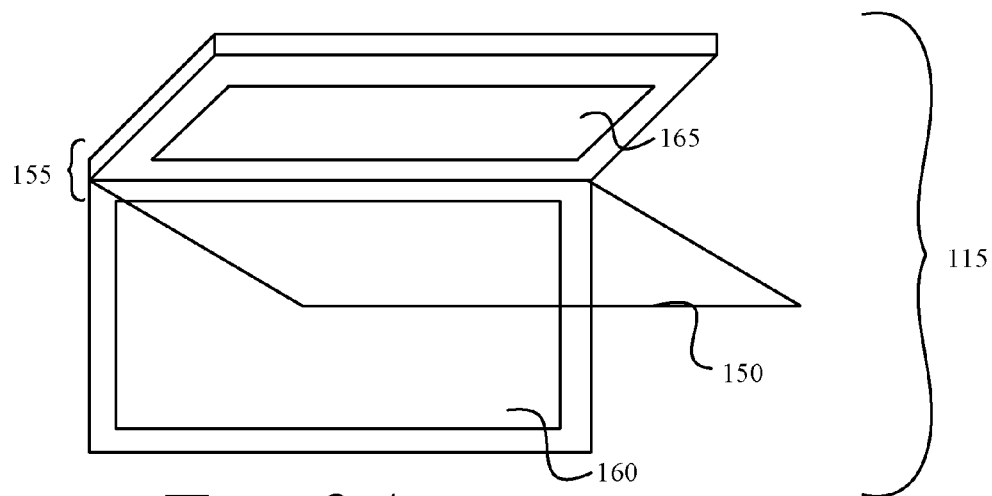
FIGS. 2A-2B depict an embodiment of a viewing system for viewing images.
Figure 2B:
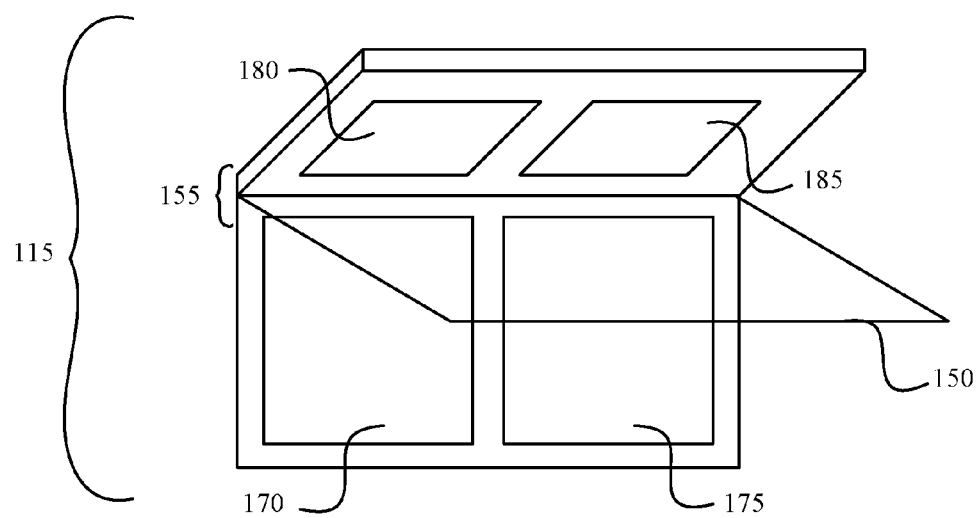

Still referring to FIG. 1, included within the environment 100 is a viewing apparatus 115 that, in one embodiment, is the viewing apparatus 115 illustrated in FIG. 2A and FIG. 2B. Other embodiments include a viewing apparatus that includes any of the following display devices: an LCD monitor; a CRT monitor; a plasma display; a surface-conduction electron emitter display; an organic LED display; or any other medium able to display the system and method herein described.

While the above embodiments contemplate an environment 100 that includes devices able to capture images of organs included within the body, other embodiments may include an environment 100 with an imaging machine 105 and other components necessary to capture images of external features of the body such as the skin. In other embodiments, the environment 100 includes an imaging machine 105 and related environmental components necessary to capture images in any of the following contexts: oil exploration; improvised explosive device detection and other bomb detection; identification of human bodies within vehicles and other transportation devices; mining; security applications such as body cavity searching, baggage searching, and other security-based searching; detection of underground facilities; cargo tracking to track the contents of cargo containers; and forms of medical imaging for various organs such as the breast, and the prostate.

Other embodiments of the environment 100 include a computing machine 120 and viewing apparatus 115 able to network with clients on the network 110 such that the clients on the network 110 may remotely view the images generated by the imaging machine 105, and may further view the images displayed on the viewing apparatus 115. In this embodiment, the end user may have a substantially similar viewing apparatus to the viewing apparatus 115 in communication with the computing machine 120, and so may have the ability to view stereo imaging of the restructured breast volume generated by the imaging machine 105 and formatted by the methods and systems herein described. Further embodiments include remote viewing capabilities that provide an end user with the ability to interact with the slices generated by the imaging machine 105 in a manner similar to that of the methods and systems herein described.

Illustrated in FIGS. 2A and 2B are embodiments of a viewing apparatus 115 included within the environment 100 depicted in FIG. 1. Each of FIGS. 2A and 2B illustrate a viewing apparatus 115 that includes display units connected at a joint 155 and attached to a beam splitter 150. Depicted in FIG. 2A is an embodiment of a viewing apparatus 115 that includes a top display unit 165 connected to a bottom display unit 160 at a joint 155 that spans the width of each display unit 160, 165. The display units 160, 165 are further connected to a beam splitter 150. Depicted in FIG. 2B is an embodiment of a viewing apparatus 115 that includes a left top display unit 180, a right top display unit 185, a right bottom display unit 175, and a left bottom display unit 170; where each of the top display units 180, 185 are connected to each of the bottom display units 170, 175 via a joint 155 that spans the combined width of each top display unit set and each bottom display unit set. A beam splitter 150 is connected to each of the display units such that the beam splitter 155 spans the combined width of the left and right top display units 180, 185, and the combined width of the left and right bottom display units 170, 175. The display units 170, 175, 180, 185 are further connected via a joint 155 that spans the width of the beam splitter 150.

Further referring to FIGS. 2A and 2B, and in more detail, in one embodiment each included display unit 160, 165, 170, 175, 180, 185 is a Dome E5 AMLCD flat-panel 21.3 inch grayscale monitor. Other embodiments include display units that can be any of the above described display devices. Still other embodiments include display units that include any of the following: a five mega pixel display device; a display device able to display at a resolution of 2560 to 2048 pixels; a sixteen mega pixel display device; or any other display device with a resolution able to display the images generated by the imaging device 105. In another embodiment, each display unit is configured to emit a polarized image, where the polarization axes of the two monitors are orthogonal to each other. The viewing apparatus 115 can, in some embodiments, include display units configured to emit a polarized image, where the display units employ circular polarization techniques such that the orthogonal directions are clockwise and anti-clockwise.

Embodiments include a beam splitter 150 that has a glass plate coated with half-silvered coating that is approximately fifty percent transmissive and fifty percent reflective. In this embodiment, the beam splitter extends out from the joint 155 connecting the top display unit(s) to the bottom display unit(s). The beam splitter 150 bisects the angle created at the joint 155 connecting the top display unit(s) to the bottom display unit(s), and can be movably rotated about the joint 155 to provide a direct view of either the top display unit(s) or the bottom display unit(s). In this embodiment, the beam splitter 150 operates to reflect the image projected by the top display unit(s) 165, 180, 185, and transmit the image projected by the bottom display unit(s) 160, 170, 175. The beam splitter 150 maintains both the transmitted and reflected image so that a user viewing the beam splitter 150 through polarized glasses where the lenses of the glasses are cross-polarized, may see a three dimensional representation of the image. This occurs when the user's visual system fuses the reflected image from the top display units as viewed through one eye, with the transmitted image from the bottom display units as viewed through the other eye. The single fused image produces a three dimensional view of a stereo pair of two dimensional projection images of either a volumetric set of data or a physical volume. Other embodiments include a beam splitter 150 that can be locked in a single position so that a user may directly view the lower display unit(s) 160, 170, 175.

Referring to FIG. 2A, and in more detail, in one embodiment, the viewing apparatus 115 includes a single top display unit 165 and a single bottom display unit 160. Each display unit 160, 165 is configured to display the reconstructed two dimensional images, stereo pair of projection images or image slices generated by the imaging device 105. In one embodiment, the display units 160, 165 may display a single reconstructed image of the volume, organ or other object; while in other embodiments the display units 160, 165 may display multiple views of a displayed two dimensional projection image, or stereo pair of images. Further embodiments include display units 160, 165 able to display two different projection images, a stereo pair of images, or image slices. In this embodiment, a first displayed image or stereo pair of images corresponds to a recent, younger or current view of the displayed volume, object or organ; while a second displayed image or stereo pair of images corresponds to a view of the displayed volume, object or organ that is older than the recent, younger or current view. Differences between the older image of the volume, object or organ, and the current image of the now older volume, object or organ may be highlighted using a pixel comparison or other comparison algorithm. This embodiment is of particular use when illustrating the effects of change, aging and time on the volume, object or organ; or to illustrate development or recession of changes, growths, cancer or another disease. Such an embodiment may be used in another embodiment to compare an image representative of a recently captured volume, object or organ image to a test image. This embodiment may be used as a method for teaching operators, users of the systems and methods described herein, doctors or other medical associates how to identify tumors, illnesses, or other structures, densities, or elements within an image.

Referring to FIG. 2B, and in more detail, in one embodiment the viewing apparatus 115 includes a left top display unit 180 connected to a right top display unit 185, and a left bottom top display unit 170 connected to a right top display unit 175. Together the left and right top display units create a single top display unit, while together the left and right bottom display units create a single bottom display unit. In one embodiment, the multiple display units can be used to display either different views of the same volume, object or organ, or differing views of different volumes, objects or organs. As described above, these multiple display methods can be used to display the effects of time, changes, aging, cancer, disease, lack of disease, comparison to a test case, or other contrasting view of a same or different volume, object or organ to further identify points of interest within either or both of the displayed sets of images, or images. Other embodiments of the viewing apparatus 115 include more than two top and/or bottom display units. Still other embodiments of the viewing apparatus 115 include the ability to display animation of a displayed image, stereo pair of images or set of images.

Further referring to FIGS. 2A and 2B, a viewing apparatus 115 includes a joint 155 installed between top display units and bottom display units. In one embodiment, the joint 155 is a hinge movable about a central axis, so that the angle between the top display units and the bottom display units may be altered. Other embodiments of the viewing apparatus 115 include an apparatus 115 driven by a graphics controller card (not shown.) In one embodiment, the graphics controller card (not shown) that has onboard memory such that the graphics card can render a stereo projection through a moving slab of slices in real time, and further allow a user to alter the point of view within the stereo mode.

In one embodiment, the viewing apparatus 115 can be any stereo displaying systems, such as the following devices manufactured by Planar Systems: the SD1710 Stereoscopic 3D Display; the SD2020 Stereoscopic 3D Display; the SD2420W Stereoscopic 3D Display; and the SD2620W Stereoscopic 3D Display. Other embodiments include a stereoscopic three dimensional display created using the Planar Systems Dome Z16 display.

Still other embodiments include a viewing apparatus 115 that employs methods of displaying which include rapid temporal alternative of two images, where each image is a member of a stereo pair of images. In this embodiment, the viewing apparatus rapidly and temporally alternates display of the stereo pair of images in synchronization with a user's electronic shutter glasses. In another embodiment, the viewing apparatus 115 includes an auto stereoscopic display where two images, where each image is a member of a stereo pair of images, are individually directed towards a user's eyes such that the user can view the stereo pair of images as a three dimensional image without the need for an additional viewing apparatus such as stereo glasses. Other embodiments include a viewing apparatus 115 that employs any other type stereo display technology or viewing method that permits an end user to view a three dimensional image from a stereo pair of images with or without the aid of an additional viewing apparatus.

Figure 3:
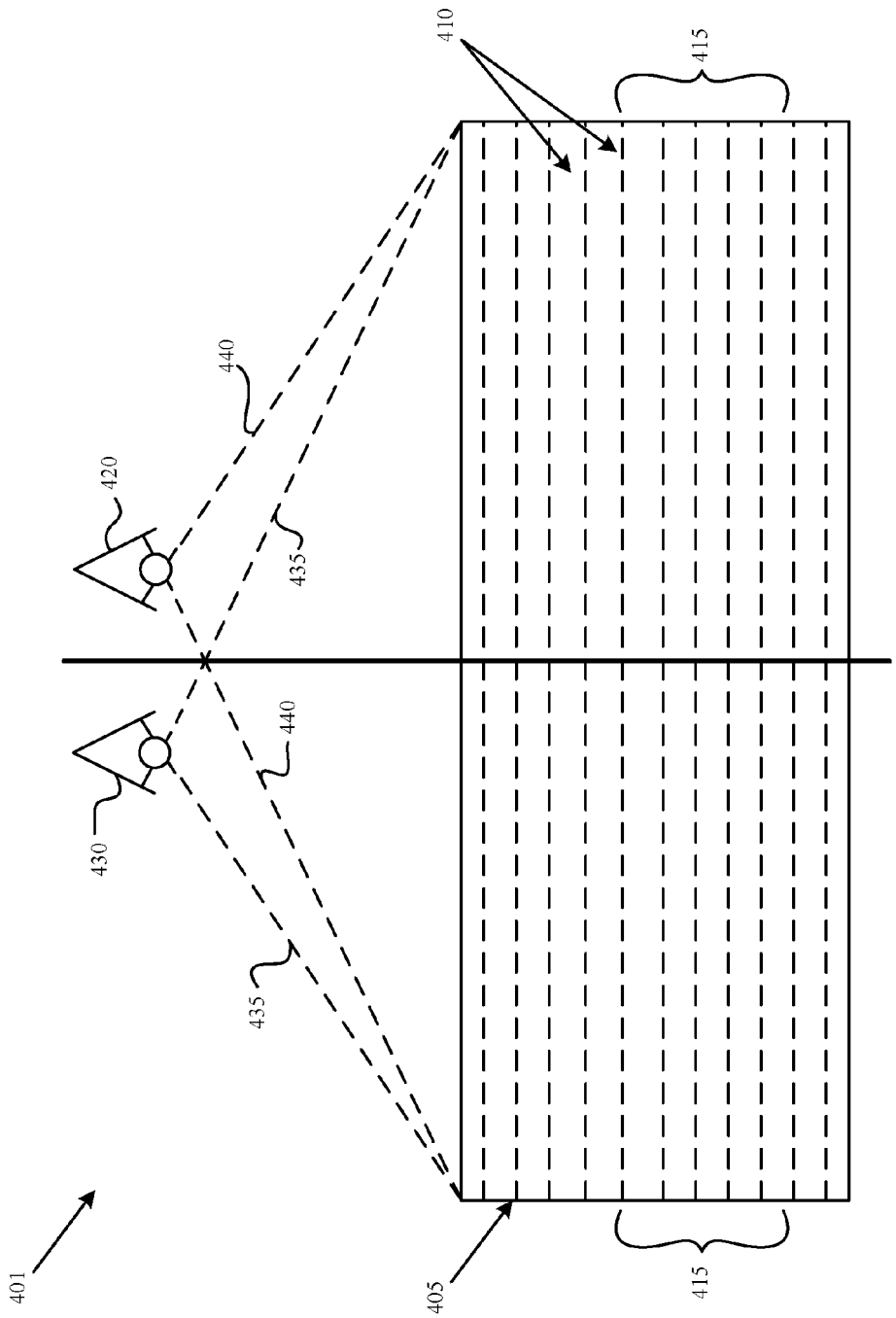
FIG. 3 depicts an embodiment of a system for generating a stereo view of collected images.

Illustrated in FIG. 3, is an embodiment of a system for generating a stereo view of a stereo pair of two dimensional images representative of a physical volume or a volumetric set of data. In this system 401, the stereo pair of two dimensional images or image slices, are compiled into a single reconstructed volume 405. Within the volume 405 is a collection of two dimensional images or a slab of slices 415 that are included within a projection set, and that contain images of either a physical volume or a volumetric set of data. Views of the reconstructed volume 405 are taken from a first point of view 430 with a first line of sight 435, and a second point of view 420 with a second line of sight 425.

Further referring to FIG. 3, and in more detail, using two dimensional projection images of the reconstructed volume 405, a first projection image is generated from a first point of view 430 while a second projection image is generated from a second point of view 420 to create a stereo pair of images. This stereo pair of images, when viewed through a stereo viewing apparatus, provides a three dimensional view of a portion of the volume 405. In one embodiment, the first point of view 430 and the second point of view 420 are separated by a distance within the range of 0 to 10 centimeters. Other embodiments include spacing between each point of view substantially greater than, equivalent to, or less than a value representative of an average distance between a human pair of eyes. Further embodiments include a first and second point of view 430, 420 that are located parallel to each other so that the view from each point results in a visually correct pair of stereo images. Other embodiments include a first and second point of view 430, 420 directed toward a common focal point according to the camera toe-in method. In this embodiment, the vertical parallax created by directing the view points towards a single focal point may result in visual discomfort.

In one embodiment, creation of the stereo pair of images includes constructing two projection images from a slab of slices, where each projection image is calculated from the volumetric set of data or physical volume represented by images, and where each image is taken from a separate and distinct viewpoint. One embodiment includes determining a stereo pair of images by calculating a first projection image from the first point of view 430, and then calculating a second projection image from the second point of view 420. Each image is calculated using ray tracing in conjunction with a weighting function to pass a virtual ray through the volumetric data represented within the slab, to weight the value of each of the pixels encountered in successive slices as the ray passes through the slab in constructing the two dimensional projection image. Different weighting functions may be employed, including, but not restricted to: linear averaging; depth-weighted averaging; maximum intensity projection; or any other appropriate weighting function. In some embodiments, the identified weighted pixel values are used to construct a two dimensional image representative of a view of the volumetric set of data from either the first or second point of view. The created two dimensional images display pixels at a brightness that correlates to each pixel identified from each images respective point of view.

Other embodiments include a recalculation of the displayed stereo pair of images when the point of view of the stereo image changes in response to a tilt command and/or in response to user input indicating that the point of view should be changed. In this embodiment, the change in point of view causes each of the points of view 430, 420 to change such that each point of view identifies a different set of points within the volumetric data represented by the slab. The change in the point of view requires that the displayed two dimensional images to be re-calculated using ray tracing and using the weighting function. What results is a different pair of stereo images representative of a viewpoint of the volumetric image data represented by the slab that differs in a manner substantially in accordance with the user-specified change in point of view or tilt.

In still another embodiment, the system described in FIG. 3 can be used to generate a stereo view of images obtained from an imaging machine able to obtain images of any of the following: a physical volume, external features of the human body or of any other living organism; images generated in relation to oil exploration; images of an improvised explosive device or any other images generated during bomb detection; identification of human bodies within vehicles or other transportation devices; images generated by security applications that perform body cavity searching, baggage searching, or any other security detection process; detection of underground facilities; images generated during cargo tracking to track the contents of cargo containers; or any images generated by any device capable of generating internal and/or external images of the human body. In such an embodiment, the images generated are images of a three dimensional volume.

Figure 4A:
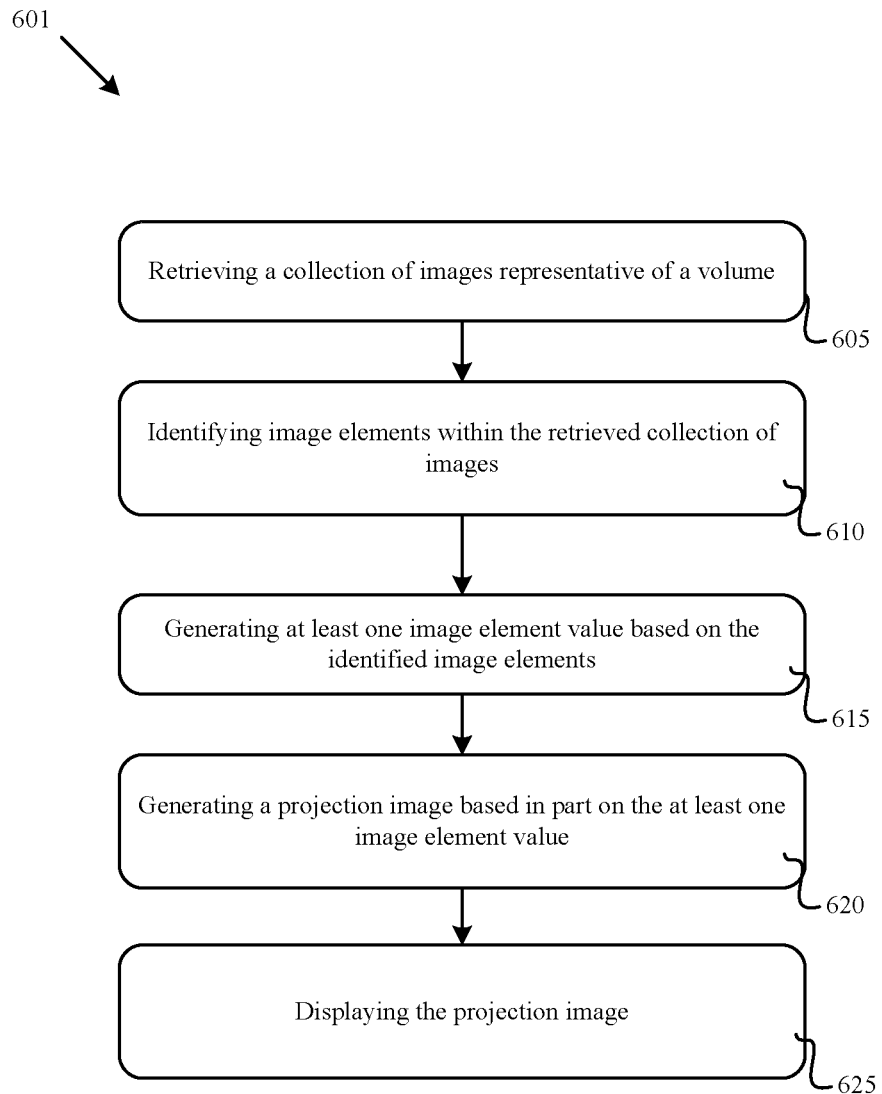
FIGS. 4A-4B are illustrative flow diagrams of an embodiment of a method for displaying images.

Illustrated in FIG. 4A is one embodiment of a method 601 for three dimensional viewing the method 601 including retrieving a collection of images representative of a volume (step 605). Within the retrieved collection of images, image elements are identified (step 610). At least one image element value is generated, where the image element value is based on the identified image elements (step 615). A projection image is generated, where the projection image is based in part on the at least one image element value (step 620). The generated projection image is then displayed (step 625).

Further referring to FIG. 4A, and in more detail, retrieving a collection of images representative of a volume (step 605) can include retrieving a collection of images generated by the imaging machine 105. Other embodiments of the method 601 can include retrieving a collection of images from a storage repository located on the computing machine 120 or on any other computing machine or device in communication with either the computing machine 120 or the imaging machine 105. In one embodiment, the collection of images includes a single image, where in another embodiment, the collection of images includes more than one image.

Image elements are identified by a computing machine 120 from within the collection of images (step 610) retrieved by the imaging machine 105 or from a storage repository. In one embodiment, image elements are identified by executing a ray tracing function to identify image elements along a path that passes through the collection of images. Within this embodiment, the collection of images can include a sequentially ordered stack of images. The path is directed through the sequentially ordered stack of images, and is directed using any one of a parallel axis, an asymmetric frustrum, a camera toe-in, or a perspective projection. In still another embodiment, the computing machine 120 is further configured to apply a weighting function to intensity values that are related to the identified image elements. Other embodiments include applying a weighting function, where the weighting function can be any one of a pixel density averaging function; a depth-weighted function; a maximum intensity projection function; or any other weighting function able to identify image elements able to be used within the methods and systems described herein.

Using the identified image elements, the computing machine 120 is further able to generate at least one image element value (step 615). In one embodiment, the generated image element value is associated with the path and based in part on the results of the execution of the ray tracing function and the results of the application of the weighting function.

In one embodiment, the computing machine 120 generates a projection image that is based on the at least one image element value (step 620). Other embodiments include a computing machine 120 that generates a stereo pair of projection images from the at least one image element value. The stereo pair of projection images is generated by executing the ray tracing function from two different points of view and along two different paths, where each path originates from one of the two different points of view. This embodiment can include generating a collection of stereo pairs of projection images.

In another embodiment, the viewing apparatus 115 displays the generated stereo projection image(s) (step 625). The projection images can be sequentially displayed by stepping through the collection of retrieved images. In one embodiment, the display conditions can be adjusted when the projection image(s) are displayed. Examples of display conditions that can be adjusted include: a pixel intensity transfer function, slab thickness, viewing mode, point of view, or any other display condition able to be adjusted by the systems and methods described herein. Methods of displaying the stereo pair of projection images include removing a pair of stereo images from the collection of stereo images and adding a new pair of stereo images. In this method the pair of stereo images that is added is a subsequent pair of stereo images in the sequence of images within the collection of stereo image pairs. Other embodiments include displaying the projection images in a non-stereo single slice viewing mode, a non-stereo cine mode or a non-stereo slab viewing mode.

Figure 4B:
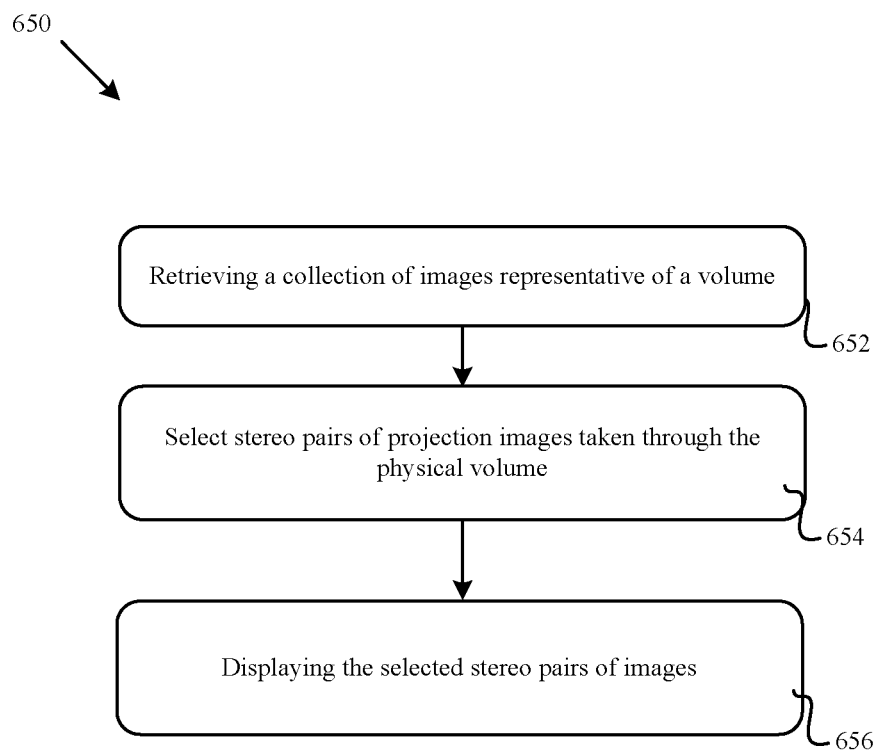

Illustrated in FIG. 4B is another embodiment of a method 650 of three dimensional viewing. The method 650 includes retrieving a collection of images representative of a volume (step 652), selecting a stereo pair, or stereo pairs, of projection images taken through a physical volume (step 654), and displaying the selected stereo pair(s) of images (step 656).

Further referring to FIG. 4B and in more detail, retrieving a collection of images representative of a volume (step 652) includes using the imaging machine 105 to retrieve images representative of a physical volume. In one particular example, this includes using an x-ray machine to obtain a collection of x-ray images of a physical volume. Still other embodiments include using any imaging machine 105 able to obtain images of a physical volume to obtain a collection of images representative of that physical volume.

In one embodiment, stereo pairs of projection images are selected from the retrieved collection of images (step 654). Pairs of projection images are selected based on whether the images, when viewed through a stereo viewing apparatus, provided a displayed image of a three dimensional volume.

Other embodiments include displaying the selected stereo pair(s) of images (step 656) on a stereo viewing apparatus such as those described above.

In one embodiment of either of the above-described methods 601, 650, a cursor is provided that can be positioned within an image to identify a location within a projection image. The cursor can, in one embodiment be a stereo cursor, or a shape comprised of a number of pixel elements. The shape, for example, might be an arrow, a circle or square or even a 3-dimensional shape such as an outline cube. In one embodiment, the shape can be drawn in both a first and second projection image. The vertical coordinate of corresponding elements in the two shapes can be the same in each of the two projection images, while the horizontal coordinate of corresponding elements in the two shapes may differ, depending upon their intended perceived location in depth. Corresponding elements with identical horizontal coordinates will be perceived to lie at the surface of the display device. Those for which the horizontal coordinate for the cursor as seen by the right eye is to the left of that seen by the left eye can be perceived to lie in front of the surface of the viewing apparatus 115. Those for which the horizontal coordinate for the element seen by the right eye is to the right of that seen by the left eye can be perceived to lie behind the surface of the viewing apparatus 115. In either case, the perceived distance from the display surface can be proportional to the degree of disparity between the two horizontal coordinates. The perceived horizontal location of the cursor in stereo can be midway between the horizontal coordinates of the cursor as drawn within each image member of the pair of stereo images. The perceived vertical location of the cursor in stereo can be at the shared vertical coordinate.

If an identical cursor is drawn in both projection images, displaced by a horizontal distance value but positioned at substantially the same vertical coordinate, then the cursor can be perceived to lie in a plane parallel to the display surface, at a depth determined by the amount of horizontal disparity. Moreover, it is possible to draw a three-dimensional cursor by shifting different elements of the cursor by different amounts horizontally according to the desired depth location of each aspect of the cursor.

The location of the stereo cursor in the perceived volume resulting from the displayed stereo projection images, can be interactively controlled by a user via an input device 125 connected to the computing machine 120. For example, using an input device 125 such as a mouse, the horizontal and vertical location of the cursor can be controlled by horizontal and vertical movements of the mouse. The location of the marker in depth can be controlled by rotation of the mouse scroll wheel. This capability also makes it possible for the user to make length and volume measurements in the displayed volume. By using the stereo cursor to mark two locations by placing markers in the volume, possibly at different depths in the volume, an application executing on the computing machine 120 would be able to calculate the distance between two or more placed markers Similarly, by using the stereo cursor to mark additional locations around some region in the volume, an application executing on the computing machine 120 would be able to estimate a value representative of volume contained by the marked locations. These calculations could further be translated into coordinates, distance values, area values, volume values, or any other measurement or descriptive representative of the region, space or location tagged by the placed marker(s).

The location of the stereo marker in the displayed volume can also be controlled by some other agent. For example, Computer-Aided Detection (CAD) software analyses may be used with mammographic or other medical images to identify potential regions of abnormality. Currently, these are indicated to the radiologist by placing markers on the two dimensional projection images. In the case of stereo imaging, software could correlate regions identified independently in the two images and, for corresponding regions, place a stereo marker at the appropriate location in each image. This would be perceived to mark the region not only by its horizontal and vertical location, but also in depth.

In one embodiment, the cursor can be positioned to identify a section of the projection image(s). In another embodiment, two cursors can be positioned to identify a section of the projection image(s). The distance between each of the cursors can be measured either by a user or automatically via an application executing on the computing machine 120.

Alternatively, the CAD application could be used to mark and display all elements or regions it finds of interest in each of the two images of the stereo pair. Two visual methods could be employed by the user to identify likely false positives, i.e., those elements or regions marked by the CAD algorithm in one of the images but not in the other. The first depends on the appearance and location in depth of marked elements or regions. A CAD-marked element or region that has no correspondent in the other image will have a shimmering appearance in the perceived stereo image due to binocular rivalry and will visually appear to lie at the surface of the display as though the element or region has zero horizontal disparity. This method can be effective when the volumetric structure being displayed in stereo is located behind or in front of the display surface, thereby segregating in depth the non-corresponding elements and regions from those that do have a correspondence.

The second visual method for identifying non-corresponding elements or regions marked by a CAD application uses temporal oscillation of the lateral position of the two images in the stereo display. If the position of each image undergoes a small amount of sinusoidal oscillation horizontally in the stereo display, with the oscillation 180 degrees out of phase for the two images, then corresponding elements or regions within the fused stereo image will be perceived by a user to oscillate back and forth in depth, with no change in position horizontally or vertically. On the other hand, non-corresponding elements or regions, since they are seen by only one eye, will be perceived to lie at the screen surface and to oscillate laterally and not in depth. The difference in horizontal versus in-depth oscillations will segregate and distinguish between CAD marks for corresponding and non-corresponding elements and regions. This method may be applied only to the CAD-positioned marks, leaving the two images comprising the stereo pair static. In this case the marks only undergo a small amount of sinusoidal oscillation horizontally in the stereo display, with the oscillation 180 degrees out of phase for the two images. Corresponding marks in the two images will be perceived to oscillate back and for the in depth, with no change in position horizontally or vertically, while a mark with no correspondent in the other image will be perceived to oscillate laterally and not in depth.

Figure 5A:
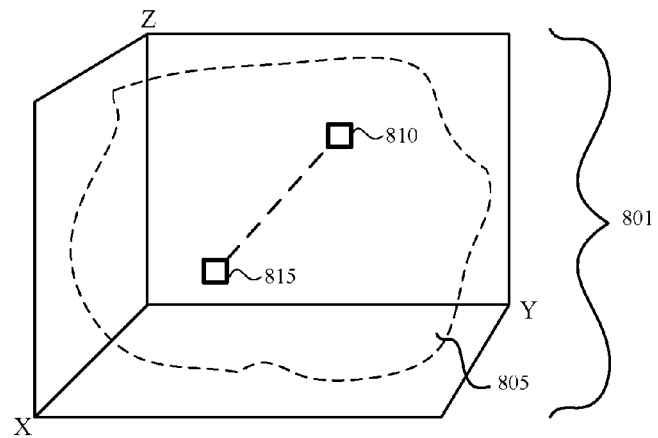
FIGS. 5A-5C depict an embodiment of a system for marking stereo pairs of images.
Figure 5B:
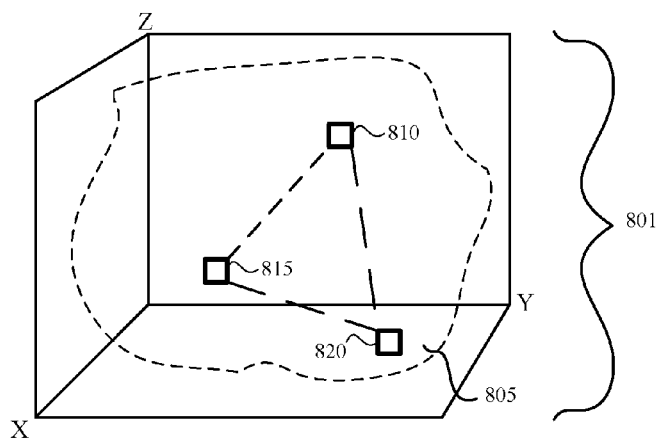
Figure 5C:
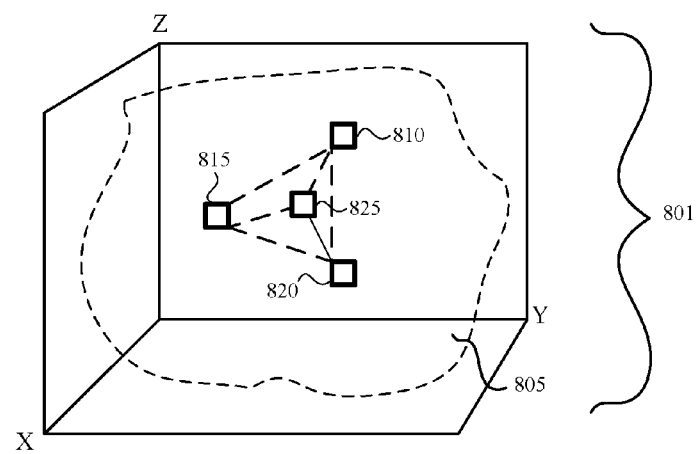

Illustrated in FIGS. 5A-5C is a system for marking a perceived three dimensional image. Each figure illustrates a three dimensional space 801 having three axis of measurement, i.e. an X axis, a Y axis and a Z axis. Within the three dimensional space 801 is a perceived three dimensional image 805 having dimensions measurable on each of the X axis, the Y axis and the Z axis. Placed within the perceived three dimensional images 805 are a first marker 810 and a second marker 815, as shown in each of FIGS. 5A, 5B and 5C. Further placed within the perceived three dimensional images 805 is a third marker 820 as is shown in FIGS. 5B and 5C. Still further placed within the perceived three dimensional images 805 is a fourth marker 825, as shown in FIG. 5C. In some embodiments, placed within the perceived three dimensional images 805 are four or more markers.

Still referring to FIGS. 5A-5C, and in more detail, the three dimensional space 801 has, in one embodiment, three axes of measurement. The axis of measurement can in one embodiment be marked as the X axis, the Y axis and the Z axis. In other embodiments, the axis can be marked using alternative letters, numbers or identifiers. Still other embodiments include axes that are unmarked. Coordinates of images displayed within the three dimensional space can be measured using any one of the following coordinate systems: Cartesian; cylindrical; spherical; parabolic; polar; or any other coordinate system that comports with the systems and methods described herein.

In one embodiment, illustrated in FIGS. 5A-5C is a perceived three dimensional image 805 having dimensions that are measurable along three axis of measurement. Other embodiments include a perceived image 805 that is measurable along two axis of measurement. In one embodiment, the perceived three dimensional images 805 are created using the systems and methods described herein.

The markers 810, 815, 820 and 825 are, in one embodiment, placed using three dimensional or two dimensional stereo cursors. In still other embodiments, the three markers 810, 815, 820 and 825 can be any one of the following shapes: square; cube; arrow; circle; oval triangle; rectangle; polygon; star; rhombus; trapezoid; or any other two-dimensional or three-dimensional shape able to enclose at the very least an area. The markers 810, 815, 820 and 825 are in one embodiment three dimensional and are in other embodiments two dimensional. Embodiments can include markers 810, 815, 820 and 825 that are patterned, colored, glowing, textured or otherwise exhibiting a type of design. The markers 810, 815, 820 and 825 can be in some embodiments, a set of pixel elements that are drawn into the image 805 using an application that executes on the computing machine 120. Still other embodiments include markers 810, 815, 820 and 825 that can measure any of: the precise location of a selected element within the image 805; distances between selected elements within the image 805; contours, areas or volume defined by a set of markers or a selection of multiple elements within the image 805; or differences in selected aspects of the image 805 (for example geometries within the image 805) where the image 805 changes because of a lapse of time or the capturing of the image 805 using different imaging techniques, or under different conditions or contexts. In one embodiment one, two, three, four or more than four markers 810, 815, 820 and 825 are inserted into the image 805. Still other embodiments include markers that are uniform, meaning each marker is the same as the other markers. Other embodiments include markers 810, 815, 820 and 825 where one or more markers are different from the other markers in that they have a different: color; shape; size; design; or other identifying characteristic.

Illustrated in FIG. 5A is an example of the use of two markers 810 and 815 to select or otherwise identify a section of the perceived image 805. In one embodiment, the length extending from one of the markers 810 to the other marker 815 can be measured to obtain a value representative of the length. Measurement of the length can include obtaining the coordinates of one of the markers 810, obtaining coordinates of the other marker 815 and then using the differences in the obtained coordinates to generate a value representative of the length. Other embodiments include using a computer application executing on the computing machine 120 to automatically identify a value associated with the length. In one embodiment, the computer application uses a method similar to that described above in that the computer application obtains the coordinates of both markers 810, 815 and then calculates the differences between the coordinates to further generate a value representative of the length.

Illustrated in FIG. 5B is an example of the use of three markers 810, 815 and 820 to select or otherwise identify a section of the perceived image 805. In one embodiment, the lengths extending between markers 810 and 815, markers 815 and 820, and markers 810 and 820 can be measured to obtain values representative of the lengths. Still other embodiments include obtaining a value of the area bounded by markers 810, 815 and 820. One embodiment includes obtaining the coordinates of each of the markers 810, 815 and 820 and then using the differences between the coordinates to obtain values representative of the lengths between the markers or to obtain a value representative of the area bounded by the markers. Still other embodiments include obtaining any one of the marker coordinates, the lengths between the markers or the area bounded by the markers, automatically using a computer application executing on the computing machine 120.

Illustrated in FIG. 5C is an example of the use of four markers 810, 815, 820 and 825 to select or otherwise identify a section of the perceived image 805. In one embodiment, the lengths extending between markers 815 and 810, markers 815 and 825, markers 815 and 820, markers 810 and 820, markers 825 and 810, and markers 825 and 820 can be measured to obtain values representative of the above-described lengths. Still other embodiments include obtaining a value representative of the areas and volumes bounded by any portion of markers 810, 815, 820 and 825. In one embodiment, obtaining values representative of the areas and volumes bounded by any portion of the markers 810, 815, 820 and 825, by obtaining the coordinates of each of the markers 810, 815, 820 and 825 and then using the differences between the coordinates to obtain values representative of: lengths between the markers 810, 815, 820 and 825; areas bounded in part by the markers 810, 815, 820 and 825; or volumes bounded in part by the markers 810, 815, 820 and 825.

Figure 6:
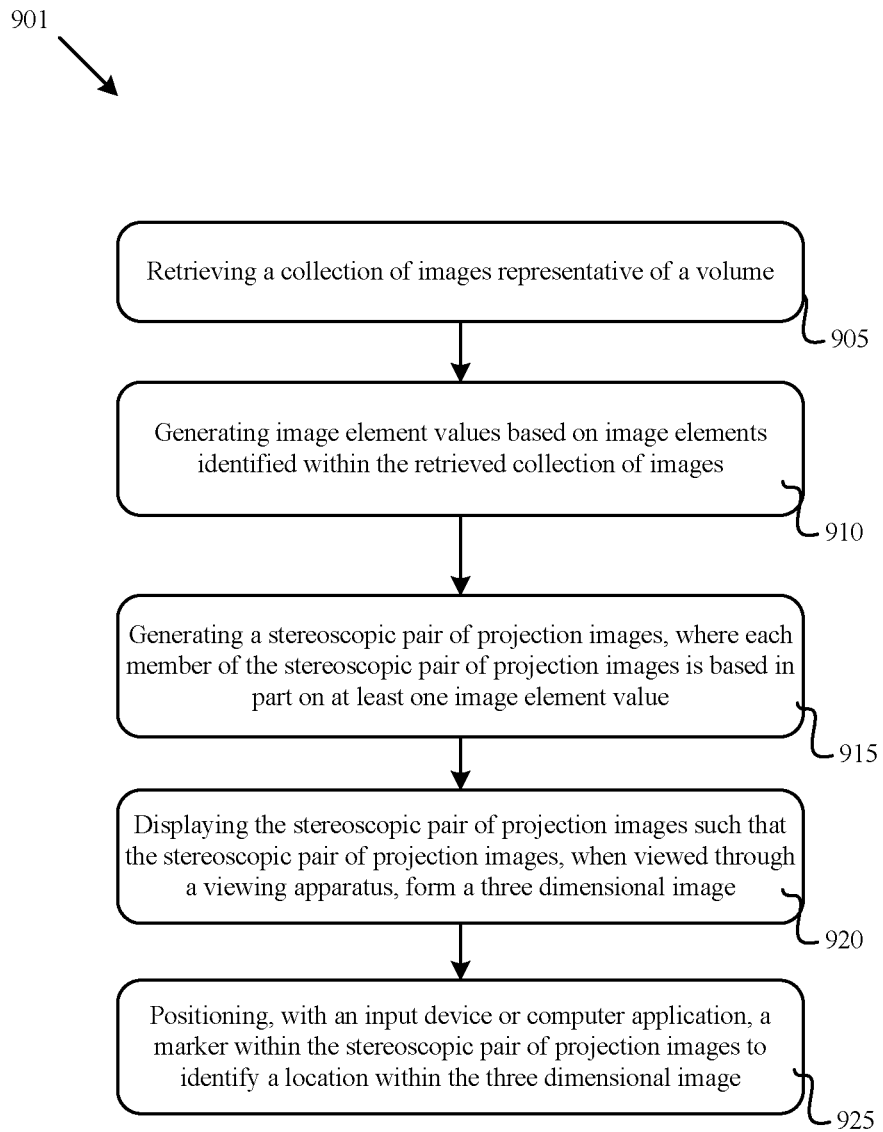
FIG. 6 is an illustrative flow diagram of an embodiment of a method for marking stereo pairs of images.

Illustrated in FIG. 6 is one embodiment of a method 901 for displaying a perceived three dimensional image. The method includes retrieving a collection of images representative of a volume (step 905), and identifying image elements within the retrieved collection of images to further generate image element values that are based on the identified image elements (step 910). A stereoscopic pair of projection images is generated, where the stereoscopic pair of projection images includes two member images, each member of the stereoscopic pair of images is based in part on at least one image element value (step 915). The stereoscopic pair of images is further displayed on a viewing apparatus such that when the stereoscopic pair of projection images is viewed through at least a portion of the viewing apparatus, a user is able to view a three dimensional image determined by the stereoscopic pair of projection images (step 920). An input device or a software application can then be used to position a marker within the stereoscopic pair of projection images to further identify a location within the perceived three dimensional images (step 925).

Further referring to FIG. 6 and in more detail, in one embodiment, a stereo cursor is used to position a stereo marker within the stereoscopic pair of projection images (step 925). Using the stereo cursor to identify a location or section of the perceived three dimensional image requires, in one embodiment, the placement of an identical cursor icon in each member of the stereoscopic pair of projection images. Thus, the positioned stereo cursor icons will have at least one coordinate in common and differ by a single horizontal coordinate. For example, the y coordinate of the positioned stereo cursor icons will have the same coordinate value; however, the x coordinate of the positioned stereo cursor icons will have a different coordinate value. Thus, a user viewing the perceived three dimensional image will perceive the horizontal location (the location along the x axis) to have a value that is midway between the x coordinate of each of the cursors, while the perceived vertical location (the location along the y axis) will have the y coordinate value shared by each of the icons. Positioning of the stereo cursor can be controlled using an input device 125 that when actuated by a user, can control the movement of the cursor along any of the axis within the three dimensional volume. In another embodiment, the placement of the stereo cursor within the perceived three dimensional images is controlled by a computer aided detection application executing on the computing machine 120. The computer aided detection application may, in this embodiment, be configured to mark and display all elements or regions identified as an element or region of interest by either the computer aided detection application or by a user.

Figure 7:
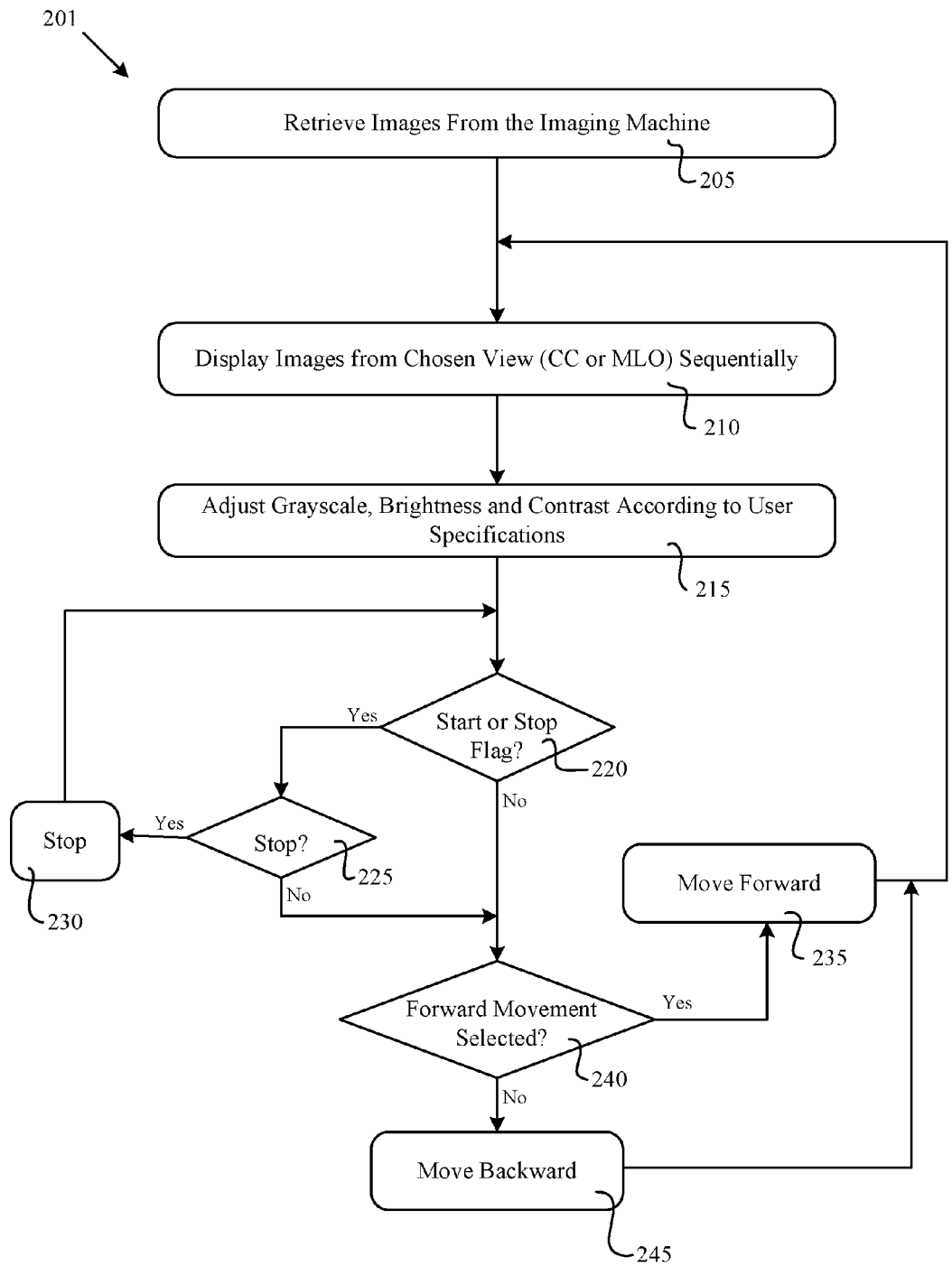
FIG. 7 is an illustrative flow diagram of an embodiment of a method for displaying a sequence of images.

Illustrated in FIG. 7 is one embodiment of a method 201 for displaying single slices from a reconstructed stack of slices created by the imaging machine 105. The method 201 includes retrieving images from the imaging machine 105 (step 205), where the images are reconstructed two dimensional images generated during scanning of an object or volumetric structure. The two dimensional images are sequentially displayed based on the user-chosen view, (e.g., either the cranio-caudal (CC) view or the mediolateral oblique (MLO) view of a breast (step 210)). Either before the slices are displayed or subsequent to when the slices are displayed, the user can invert the grayscale, adjust the brightness, and adjust the contrast (step 215). A check is performed to determine if a start or stop flag is present (step 220), and when one is present, a further determination is made as to whether or not the flag is a stop flag (step 225). If the flag is a stop flag, then display of the slices stops on the current slice (step 230). If the flag is a start flag, then movement through the stack of two dimensional slices continues in a chosen direction. The direction of movement is determined (step 240), and the slices are either displayed in forward motion (step 235) or backward motion (step 245) depending on the movement direction determination.

Further referring to FIG. 7 and in more detail, in one embodiment the method 201 retrieves the two dimensional stack of images from the imaging machine 105. Other embodiments, when the method 201 is executed on the imaging machine 105, the two dimensional stack of images is present on the machine 105 executing the method 201. In this embodiment, the method 201 can retrieve the stack of slices from a persistent or non-persistent memory location, or may process the stack of slices substantially instantaneously to provide substantially real-time data output to the viewing apparatus 115 as the slices are generated by the imaging machine 105.

In one embodiment, a user-selected view determines which view can be displayed on the viewing apparatus 115 (step 210), as well as the settings for grayscale, brightness, and contrast (step 215). A default view, in some embodiments, may be available such that when the viewing apparatus 115 displays a stack of slices, the default view (e.g., either the CC or the MLO view) can always be displayed first. Further embodiments include a viewing apparatus 115 with two bottom display units, where one display unit displays the stack of slices corresponding to one view (e.g., the CC view), and the other display unit displays the stack of slices corresponding to a different view (e.g., the MLO view). Still other embodiments allow the user to alter the contrast, brightness, and to invert the grayscale at any point during viewing.

Embodiments of the method 201 can display the slices in cine mode, and allow the user to stop the continuous display of the slices (step 230). When stopped, the last viewed slice remains on the screen until a start flag is detected (step 220). Movement forward (step 235) and backward (step 245) through the stack can be done, in some embodiments, slice-by-slice; while in other embodiments, movement can be done more than one slice at-a-time. Still other embodiments of the method 201 may perform substantially similar functionality, but utilize different steps to carry out the method 201.

Figure 8:
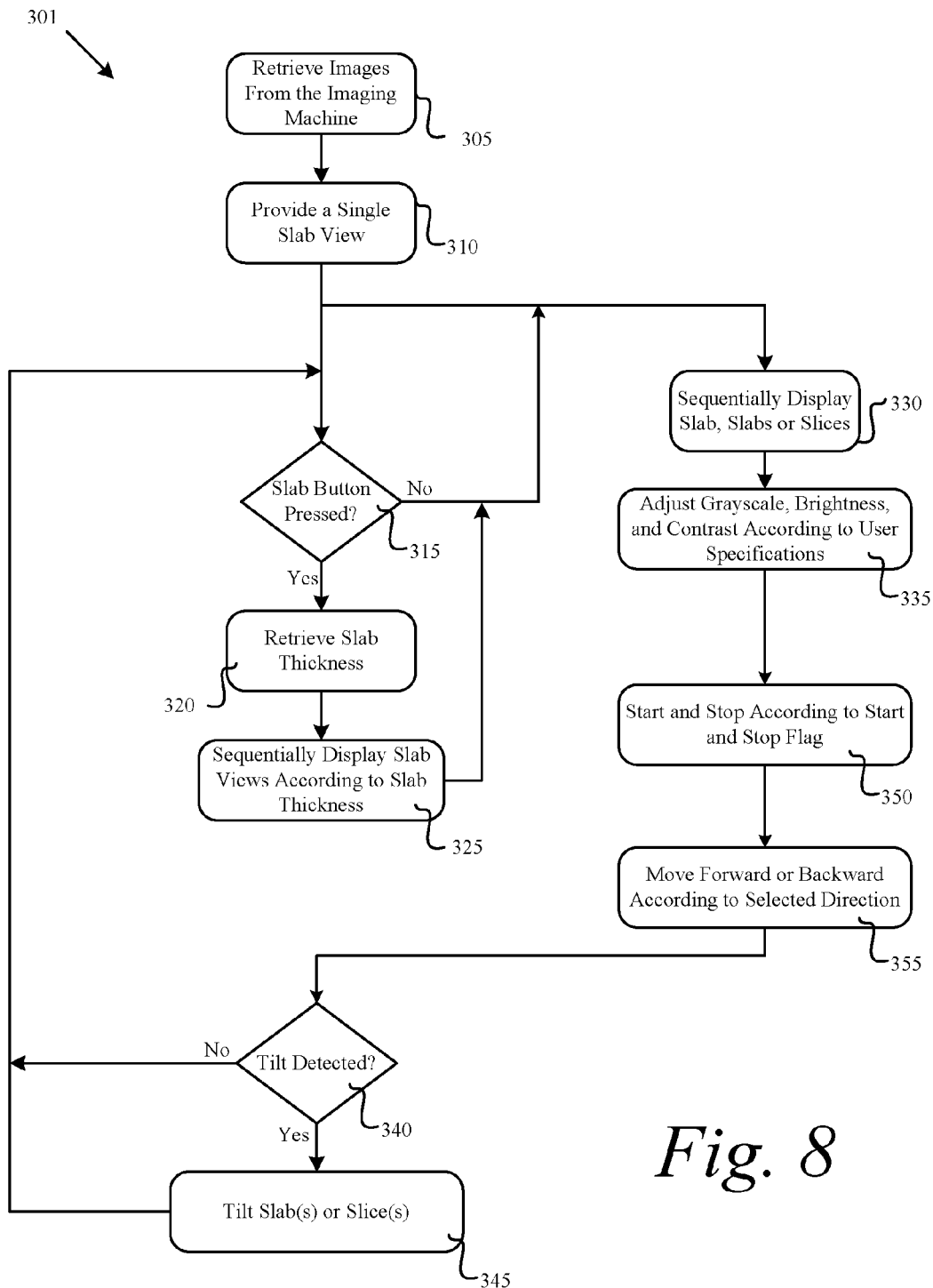
FIG. 8 is an illustrative flow diagram of an embodiment of a method for displaying a slab of images.

Illustrated in FIG. 8 is a method of 301 of providing a non-stereo slab viewing condition. Images are retrieved from the imaging machine 105 (step 305) and initially displayed as a single slab such that the view provided is a non-stereo projection view through the entire stack of slices, meaning the entire set of volumetric data provided by the imaging machine 105, (step 310). When this initial composite view of the entire set of volumetric data is displayed (step 330), the grayscale, brightness, and contrast can be adjusted according to user specifications (step 335). Due to the composite nature of the initial slab view, movement through the slices is not possible and so a determination is made as to whether a tilt command is detected (step 340). If a tilt command is detected, the slab is tilted according to the change in point of view inputted by the user (step 345). Once the slab is tilted, or if no tilt command is detected (step 340), a determination is made as to whether or not the slab button was pressed (step 315). If the slab button was not pressed, then the composite slab view continues to be displayed (step 330). When the slab button is depressed, the user-defined or default slab thickness is retrieved (step 320). A projection view is then provided through a number of slices equivalent to the desired slab thickness (step 325). Once slab views are instituted (step 325), or in the event that the slab button is not pressed (step 315), the slab views or slices are displayed in sequential order (step 330). The grayscale, brightness, or contrast of the displayed slab view or slice is adjusted according to user specifications (step 335). Determinations are made as to whether or not a start or stop flag is present, and as to whether or not the user-specified direction of movement is forward or backward (step 355). A further determination is made as to whether or not a tilt command is detected (step 340), and when such a command is detected, the slab view or slice is tilted according to the change in two dimensional projection effected by user-input (step 345). Once a tilt has been implemented, or a determination is made that no tilt command was detected (step 340); the method 301 recursively begins again with a determination as to whether or not the slab button was pressed (step 315).

Further referring to FIG. 8, and in more detail, in one embodiment, when a set of slices is initially displayed on the viewing apparatus 115 while in non-stereo slab viewing mode; the full set of two dimensional slices, or the entire volume, is displayed as a single slab (step 310). In this embodiment, and in other embodiments where a slab composed of individual slices is displayed, the two dimensional projection images viewable through a created slab are created using ray tracing methods that require an optimal radiographic density weighting. This radiographic density weighting can, in some embodiments, include a method of weighting radiographic densities encountered along each computed ray as the ray passes through a set of slices. In this embodiment, the method of weighting radiographic densities further includes: pixel density averaging at each slice encountered by the ray; depth-weighted averaging; and maximum intensity projection. In one embodiment, the initial display of the full set of volumetric data includes displaying more than one slab versus a single slab that includes all slices. In this embodiment, the slab width is defined by a default slab width either calculated based on optimal viewing standards or predefined. In embodiments where a default slab width is defined, the default slab width or thickness can be an empirical determination arrived at by determining the optimal thickness for detecting masses and calcification clusters.

In one embodiment, a determination is made as to whether or not a slab button was pressed (step 315). When the slab button is pressed, the user is provided with a slab view of the slices created by displaying a projection through a number of slices, where the number of slices displayed corresponds to a user-defined, or default slab thickness (step 325). Other embodiments include an input device that allows the user to select the set of slices to be displayed within a single slab.

Display of the slab(s) (step 330), and movement through the slab(s) (step 355) in one embodiment includes allowing the user to move smoothly and continuously through the entire stack while each slab displays a two dimensional view of a set of slices. The movement forward or backward through the stack of slab(s) or slices (step 355) can, in some embodiments, further include deleting a previous slab/slice view and adding the next slab/slice view, where the deletion and addition can include a recalculation of the provided view so that the projection is through the next incremental set of slices. In this embodiment, the substantially instantaneous deletion and addition of the previous or next slab can conserve energy and further cause it to appear as though only a single slab view is present for viewing. Still other embodiments include movement forward or backward through the slabs where each subsequent or previous view is calculated by deleting or adding a single slice to the slab view; while in other embodiments the forward or backward movement includes deleting or adding an entire set of slices to the slab view.

In some embodiments, movement through the slab(s) or slices can be stopped and started (step 350) in response to user input indicating as such. When, in one embodiment, a user chooses to stop movement through the slab(s) or slices; the user can, while movement is stopped, perform any of the following functions: alter the thickness of the slabs (i.e. increase or decrease the thickness by either entering in a thickness value or choosing the number of slices to include in a slab); altering the brightness or contrast of the images; inverting the grayscale; reducing each slab to a single slice so that the display method can mimic that of the method illustrated in FIG. 7; or alter the point of view of the slab by issuing a tilt command. In one embodiment, the thickness of a slab is altered by actuating a control for increasing thickness, or actuating a control for decreasing thickness such that a single actuation of either control will cause the thickness of a slab to change by a single slice, while continuous actuation of either control will cause the thickness of a slab to change by a value representative of the length of time that either control was actuated. Other embodiments include a method 301 where issuance of a tilt command, alteration of brightness and contrast, and inversion of the grayscale, can be done during movement through the stack of slab(s). Still other embodiments include a method 301 where alteration of slab(s) thickness can be done substantially instantaneously while moving through the stack of slab(s).

Tilting a displayed slab (step 345), or altering the point of view of a displayed slab, changes the two dimensional projection of the slab along a chosen axis. Altering the point of view of a displayed slab can, in some embodiments, provide a view of the slab that shifts superimposed tissue out of the way so that the user can more easily view a region of interest. In one embodiment, tilting a slab can be limited to a predetermined range of angles about the z-axis. Other embodiments include a system where there is no limitation on movement or tilt of a slab, and in such an embodiment, the slab has multiple degrees of freedom such that the slab may be freely tilted about the z-axis or other axis of movement.

Figure 9:
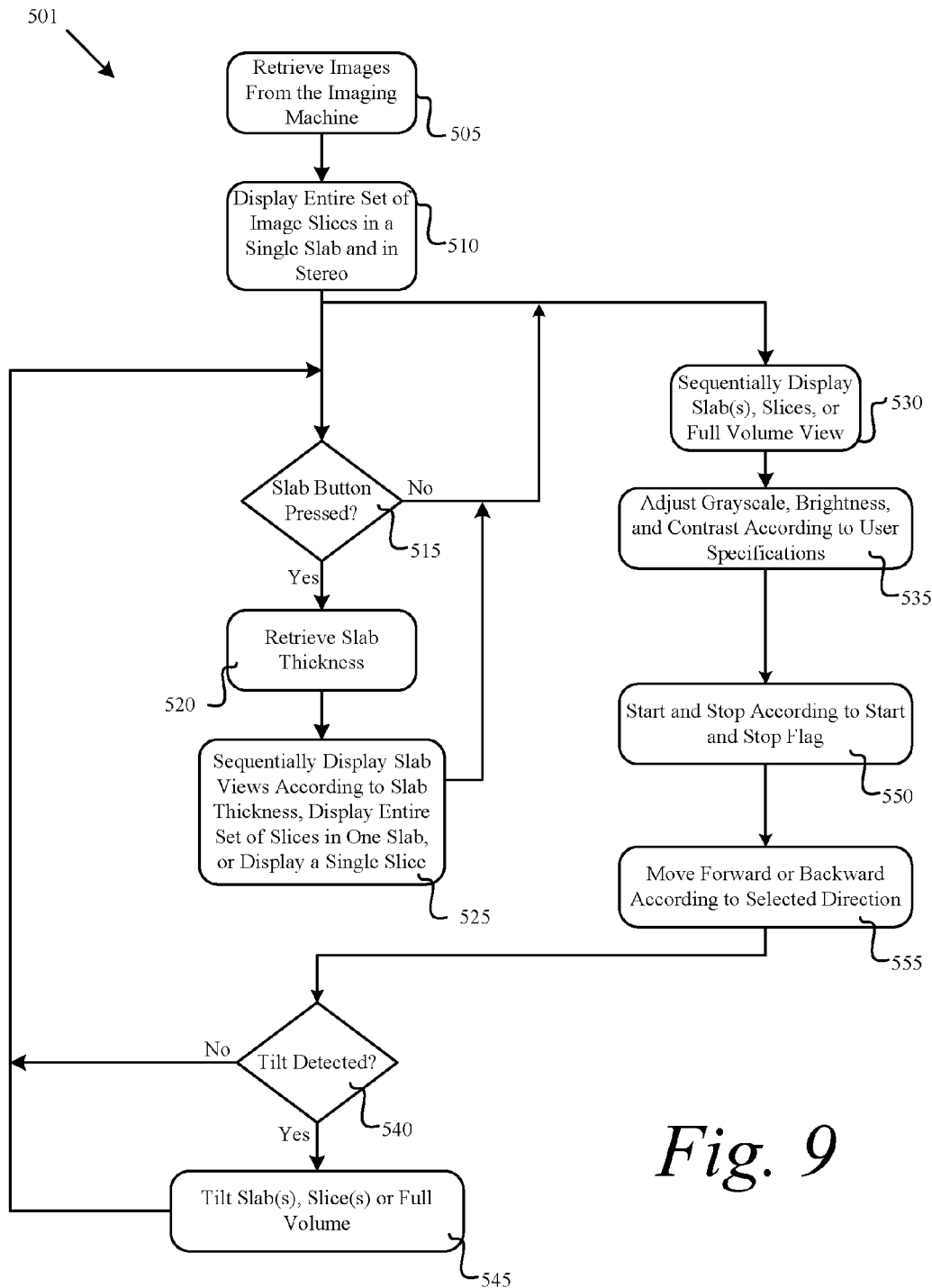
FIG. 9 is an illustrative flow diagram of an embodiment of a method for displaying a slab of images in stereo.

Illustrated in FIG. 9 is a method of 501 of providing a stereo slab viewing condition. Images are retrieved from the imaging machine 105 (step 505) and displayed as a single stereo view of the entire volume. The method 501 utilizes a pair of stereo images and the viewing apparatus 115 to provide a stereo viewing mode through the entirety of the reconstructed volume made up of the two dimensional slices as retrieved from the imaging machine 104 (step 510). This initial stereo view is displayed such that the point of view passes perpendicularly through the sequentially displayed stack of slices (step 530), and the grayscale, brightness, and contrast can be adjusted according to user specifications (step 535). Due to the composite nature of the initial stereo view, movement through the stereo image is not possible and so a determination is made as to whether a tilt command is detected (step 540). If a tilt command is detected, the point of view within the stereo image is tilted or changed according to a change in the point of view inputted by the user (step 545). Once the stereo view of the entire reconstructed volume is tilted, or if no tilt command is detected (step 540); a check is made to determine whether or not the slab button was pressed (step 515). If the slab button was not pressed, then the entire reconstructed set of volumetric data continues to be displayed (step 530). When the slab button is depressed, the user-defined or default slab thickness is retrieved (step 520). Slabs of individual slices are then viewed according to slab thickness (step 525). Once slabs are created (step 525), or in the event that the slab button is not pressed (step 515), the slabs, slices or the full volume of slices are displayed in sequential order (step 530). The grayscale, brightness, or contrast of the displayed slabs, slices or full volume of slices is adjusted according to user specifications (step 535). Determinations are made as to whether or not a start or stop flag is present, and as to whether or not the user-specified direction of movement is forward or backward (step 555). A further determination is made as to whether or not a tilt command is detected (step 540), and when such a command is detected, the slabs, slices or full volume of slices are tilted according to the change in two dimensional projection instituted by user-input (step 545). Once a tilt has been implemented, or a determination is made that no tilt command was detected (step 540); the method 501 recursively begins again with a determination as to whether or not the slab button was pressed (step 515).

Further referring to FIG. 9, and in more detail, in one embodiment, the method 501 illustrated in FIG. 9 is substantially similar to the method 301 illustrated in FIG. 8. Other embodiments include a method 501 of displaying a stereo slab view that is substantially different from a method 301 of displaying a non-stereo slab view.

When a determination is made indicating that the slab button was pressed (step 515), in some embodiments, a slab thickness can be retrieved (step 520). In this embodiment, the stereo slab view provides slab views of the image slices as opposed to a projection view through the entire volume. Slab views of the image slices are achieved by providing a projection view through a predetermined number of image slices, where the predetermined number of image slices corresponds to the slab thickness. Advantages of this embodiment include providing the user with the ability to more closely examine and select potentially suspect sections of the reconstructed volume. In other embodiments, when the slab thickness is a value of one or is some other value indicating that a single slice should be displayed, the user is shown a projection view through a single slice. Still other embodiments include detecting a slab thickness value indicating that the entire set of reconstructed volumetric data should be displayed. In this embodiment, the view displayed is a projection view through the entire set of volumetric data provided by the imaging machine 105. Embodiments of the method 501 display any one of a user selected slab, slice, or full volume sequentially (step 530), and in stereo. In embodiments where the user indicates that a single slice should be displayed, there can be no depth information available as only a single image slice is shown.

In one embodiment, a detected tilt command (step 540) or change in point of view can be inputted via the input device 125 which is connected to the computing machine 120. In some embodiments the input device 125 has a limited number of degrees of freedom and so alteration of the point of view within stereo mode involves moving the viewing to other points within the displayed image. Other embodiments where the input device 125 has multiple degrees of freedom, an alteration of the point of view within stereo mode occurs substantially instantaneously in response to an alteration of the input device's 125 position.

The above disclosure includes one or more embodiments of the methods and systems herein described. These illustrated and explained embodiments are not meant to be limiting and additional embodiments of the methods and systems herein described may be implemented using similar or functionally equivalent technology.

What is claimed is:

1. A method for marking stereo pairs of images, the method comprising:
    retrieving a collection of images representative of a volume;
    generating image element values based on image elements identified within the retrieved collection of images;
    generating a stereoscopic pair of projection images, where each member of the stereoscopic pair of projection images is based in part on at least one image element value;
    displaying the stereoscopic pair of projection images such that the stereoscopic pair of projection images, when viewed through a viewing apparatus, form a perceived three dimensional image;
    receiving, from an input device controlling a cursor within the stereoscopic pair of projection images, a first location within the perceived three dimensional image;
    automatically positioning using a computer aided detection application a first marker and a second marker within the perceived three dimensional image, each of the first marker and second marker identifying at least two second locations within the perceived three dimensional image;
        wherein the first marker and the second marker are positioned automatically via a computer aided detection application; and
    receiving, from the input device, identification of an automatically marked region of the perceived three dimensional image that, using binocular rivalry, has been identified as being contained in only one of the stereo pair of images forming the perceived three dimensional image;
    wherein the volumetric structure of the perceived three dimensional image is located behind or in front of a display surface of the viewing apparatus, and the region identified using binocular rivalry lies on the display surface of the viewing apparatus in the perceived three dimensional image.

2. The method of claim 1, wherein positioning the cursor comprises positioning at least one stereo cursor.

3. The method of claim 1, further comprising retrieving coordinates representative of the identified first location.

4. The method of claim 3, wherein retrieving coordinates further comprises retrieving, automatically via a computer application, coordinates representative of the identified first location.

5. The method of claim 1, further comprising measuring a value representative of a length extending from the first marker to the second marker.

6. The method of claim 1, comprising identification of regions contained in only one of the stereo pair of images by oscillating the lateral position of the images.

7. The method of claim 1, wherein positioning further comprises:
    positioning, using the cursor, a third marker within the perceived three dimensional images, and wherein each of the first marker, the second marker and the third marker identify at least three third locations within the perceived three dimensional image.

8. The method of claim 7, further comprising estimating a value representative of an area located within an area bounded in part by the first marker, the second marker and the third marker.

9. A system for marking stereo pairs of images, the system comprising:
    an imaging machine for retrieving a collection of images representative of a volume;
    a computing machine, in communication with the imaging machine, that:
        generates image element values based on image elements identified within the retrieved collection of images, and
        generates a stereoscopic pair of projection images, where each member of the stereoscopic pair of projection images is based in part on at least one image element value;
    a viewing apparatus, in communication with the computing machine, that displays the stereoscopic pair of projection images such that the stereoscopic pair of projection images from a perceived three dimensional image;
    an input device, in communication with the computing machine, that positions a cursor within the stereoscopic pair of projection images to identify a first location within the perceived three dimensional image,
    an application executing on the computing machine, the application configured to:
        automatically position a first marker and a second marker within the perceived three dimensional image, each of the first marker and second marker identifying at least two second locations within the perceived three dimensional image, and
        receive, from the input device, identification of an automatically marked region of the perceived three dimensional image that, using binocular rivalry, has been identified as being contained in only one of the stereo pairs of images forming the perceived three dimensional image;
    wherein the volumetric structure of the perceived three dimensional image is located behind or in front of a display surface of the viewing apparatus, and the region identified using binocular rivalry lies on the display surface of the viewing apparatus in the perceived three dimensional image.

10. The system of claim 9, wherein the cursor positioned by the input device comprises at least one stereo cursor.

11. The system of claim 9, the application automatically retrieving coordinates representative of the identified first location.

12. The system of claim 11, wherein the application is a computer aided detection application.

13. The system of claim 9, the application retrieving a value representative of a length extending from the first marker to the second marker.

14. The system of claim 9, wherein the input device further positions a third marker within the perceived three dimensional image, and wherein each of the first marker, the second marker and the third marker identify at least three locations within the perceived three dimensional image.

15. The system of claim 14, the application estimating a value representative of an area located within an area bounded in part by the first marker, the second marker and the third marker.

16. A method for marking stereo pairs of images, the method comprising:
   retrieving a collection of images representative of a physical volume;
   selecting stereo pairs of images within the retrieved collection of images;
   displaying the stereoscopic pairs of images such that the stereoscopic pairs of images, when viewed through a viewing apparatus, form a perceived three dimensional image;
   receiving, from an input device controlling a cursor within the stereoscopic pairs of images to identify a first location within the perceived three dimensional image;
   automatically positioning using a computer aided detection application a first marker, a second marker, and a third marker within the perceived three dimensional images, each of the first marker, the second marker and the third marker identifying at least three second locations within the perceived three dimensional image;
      wherein the first marker and the second marker are positioned automatically via a computer aided detection application;
   estimating a value representative of an area located within an area bounded in part by the first marker, the second marker and the third marker; and
   receiving, from the input device, identification of an automatically marked region of the perceived three dimensional image that, using binocular rivalry, has been identified as being contained in only one of the stereo pair of images forming the perceived three dimensional image;
   wherein the volumetric structure of the perceived three dimensional image is located behind or in front of a display surface of the viewing apparatus, and the region identified using binocular rivalry lies on the display surface of the viewing apparatus in the perceived three dimensional image.

17. The method of claim 16, wherein positioning the cursor comprises positioning at least one stereo cursor.

18. The method of claim 16, further comprising retrieving coordinates representative of the identified first location.

19. The method of claim 18, wherein retrieving coordinates further comprises retrieving, automatically via a computer aided detection application, coordinates representative of the identified first location.

20. The method of claim 16, further comprising measuring a value representative of a length extending from the first marker to the second marker.

21. The method of claim 16, comprising identification of regions contained in only one of the stereo pair of images by oscillating the lateral position of the marked regions in the two images, with opposing phase of oscillation in the two images.

22. The method of claim 1, wherein the region identified as being contained in only one of the stereo pair of images is has a shimmering appearance in the perceived three dimensional image.

23. The method of claim 1, wherein the region identified as being contained in only one of the stereo pair of images is a false positive.

24. The system of claim 9, wherein the region identified as being contained in only one of the stereo pair of images has a shimmering appearance in the perceived three dimensional image.

25. The system of claim 9, wherein the region identified as being contained in only one of the stereo pair of images is a false positive.

26. The method of claim 16, wherein the region identified as being contained in only one of the stereo pair of images has a shimmering appearance in the perceived three dimensional image.

27. The method of claim 16, wherein the region identified as being contained in only one of the stereo pair of images is a false positive.

* * * * *

UNITED STATES PATENT AND TRADEMARK OFFICE
CERTIFICATE OF CORRECTION

PATENT NO.       : 8,493,437 B2
APPLICATION NO.  : 12/332508
DATED            : July 23, 2013
INVENTOR(S)      : David Getty It is certified that error appears in the above-identified patent and that said Letters Patent is hereby corrected as shown below:

In the Claims

At column 22, claim number 22, line number 26, please replace "is has" with --has--

Signed and Sealed this
Third Day of September, 2013

Teresa Stanek Rea
*Acting Director of the United States Patent and Trademark Office*